US010524810B2

(12) United States Patent
Walish et al.

(10) Patent No.: US 10,524,810 B2
(45) Date of Patent: Jan. 7, 2020

(54) MEDICAL DEVICE FOR CAPTURING STONE FRAGMENTS

(71) Applicant: Gyrus ACMI, Inc., Southborough, MA (US)

(72) Inventors: Judy L. Walish, West Roxbury, MA (US); Lawrence J. St. George, Sudbury, MA (US); Tailin Fan, Nashua, NH (US)

(73) Assignee: Gyrus ACMI, Inc., Southborough, MA (US)

( * ) Notice: Subject to any disclaimer, the term of this patent is extended or adjusted under 35 U.S.C. 154(b) by 178 days.

(21) Appl. No.: 14/638,639

(22) Filed: Mar. 4, 2015

(65) Prior Publication Data

US 2016/0256179 A1 Sep. 8, 2016

(51) Int. Cl.
*A61B 17/221* (2006.01)

(52) U.S. Cl.
CPC .... *A61B 17/221* (2013.01); *A61B 2017/2212* (2013.01)

(58) Field of Classification Search
CPC . A61M 25/0074; A61M 25/00; A61B 17/221; A61B 2017/2212; A61B 2017/2215; A61B 90/03; A61B 2090/061; A61B 2090/0807; A61B 17/00; A61B 90/00
USPC .......................................................... 606/127
See application file for complete search history.

(56) References Cited

U.S. PATENT DOCUMENTS 4,611,594 A 9/1986 Grayhack et al.
7,169,154 B1 * 1/2007 Que .................... A61B 17/221 606/127
7,645,283 B2 1/2010 Reynolds et al.
7,678,119 B2 3/2010 Little et al.
8,105,334 B2 1/2012 Cheng et al.
(Continued)

FOREIGN PATENT DOCUMENTS

DE 3913936 A1 10/1990
DE 19953359 A1 5/2000
(Continued)

OTHER PUBLICATIONS

Cordes, Jens, et al. Measurement of Stone Diameter with Three Sizes of Automatically Fixating Stone Baskets, Open Journal of Urology, 2013, 3, 58-61.

*Primary Examiner* — George J Ulsh
(74) *Attorney, Agent, or Firm* — Harrington & Smith

(57) ABSTRACT

A medical device for capturing one or more stone fragments includes a sheath having a proximal end and a distal end, a handle at the proximal end of the sheath, and a basket operable with the handle. The basket includes a plurality of wires that capture the stone fragments and has a collapsed configuration when the basket is positioned within the sheath and an expanded configuration when the basket is positioned beyond the distal end of the sheath. The medical device further includes an indicator that communicates to an operator of the medical device that the size of the stone fragments exceeds a predetermined limit and a release mechanism that releases the stone fragments from the plurality of wires when the size of the stone fragments exceeds the predetermined limit. The plurality of wires are able to reset into an operable position after releasing the stone fragments.

12 Claims, 6 Drawing Sheets

(56) References Cited

U.S. PATENT DOCUMENTS

| | | | |
|---|---|---|---|
| 2002/0042617 A1 | 4/2002 | Ouchi | |
| 2002/0072764 A1 | 6/2002 | Sepetka et al. | |
| 2005/0250983 A1 | 11/2005 | Tremaglio et al. | |
| 2005/0261705 A1 | 11/2005 | Gist | |
| 2006/0247662 A1 | 11/2006 | Schwartz et al. | |
| 2008/0086149 A1* | 4/2008 | Diamant | A61B 17/221 606/113 |
| 2009/0082780 A1 | 3/2009 | Lu et al. | |
| 2010/0286709 A1 | 11/2010 | Diamant et al. | |
| 2011/0213290 A1 | 9/2011 | Chin et al. | |
| 2013/0018387 A1* | 1/2013 | Diamant | A61B 17/221 606/127 |
| 2013/0053732 A1 | 2/2013 | Heuser | |

FOREIGN PATENT DOCUMENTS

| | | | |
|---|---|---|---|
| EP | 1164945 | B1 | 10/2008 |
| EP | 991361 | B1 | 1/2012 |
| JP | 2000139933 | A | 5/2000 |
| JP | 2002113010 | A | 4/2002 |
| JP | 2003500096 | A | 1/2003 |
| JP | 2010520789 | A | 6/2010 |
| WO | WO-00/71036 | A2 | 11/2000 |
| WO | 2007109070 | A2 | 9/2007 |
| WO | WO-2008/112608 | A2 | 9/2008 |

* cited by examiner

MEDICAL DEVICE FOR CAPTURING STONE FRAGMENTS

FIELD

The present disclosure relates to a medical device. More specifically, the present disclosure relates to a medical device for capturing one or more stone fragments.

BACKGROUND

The statements in this section merely provide background information related to the present disclosure and may or may not constitute prior art.

During ureteroscopy or percutaneous nephrolithotomy (PCNL) procedures, baskets are often employed to capture and retrieve stone fragments from a patient's anatomy. After the stone fragments have been removed from the patient and released from the basket, the basket is re-inserted one or more times into the patient's anatomy to remove all or most of the remaining stone fragments. In some instances, however, stone fragments that are too large are captured in the basket, which may result in the basket getting stuck in the ureter or access sheath. If the basket can be pushed back, some fragments can be released and the basket can then be pulled out of the patient. If the basket is completely stuck, the basket can be cut apart from the basket handle and sheath, or a small laser fiber may be inserted into the patient so that laser ablation can be utilized to break up the stone fragments. In any case, if the basket damaged, a new basket has to be employed to complete the medical procedure, which may increase the surgical time and costs.

Among the literature that can pertain to this technology include the following patent documents and published patent applications: U.S. Pat. Nos. 7,645,283, 8,105,334, 7,678,119, US 2005/0261705, US 2010/0286709, DE3913936, EP1164945, and EP991361, the entire contents of which are incorporated herein by reference for all purposes.

Accordingly, to reduce surgical cost and time, there is a need for a basket that can size stone fragments during their retrieval to prevent the basket from getting stuck in the ureter or access sheath.

SUMMARY

The present invention provides an improved medical device for capturing one or more stone fragments and a method of using such a device.

In one aspect, a medical device for capturing one or more stone fragments includes a sheath having a proximal end and a distal end, a handle at the proximal end of the sheath, and a basket operable with the handle. The basket includes a plurality of wires that capture the stone fragments and has a collapsed configuration when the basket is positioned within the sheath and an expanded configuration when the basket is positioned beyond the distal end of the sheath. The medical device further includes an indicator that communicates to an operator of the medical device that the size of the stone fragments exceeds a predetermined limit and a release mechanism that releases the stone fragments from the plurality of wires when the size of the stone fragments exceeds the predetermined limit. The plurality of wires are able to reset into an operable position after releasing the stone fragments.

The medical device may be further characterized by one or any combination of the features described herein, such as, for example: the indicator is a visual indicator on a distal end of the plurality of wires; the visual indicator is a color difference that is seen by the operator of the device when the size of the stone fragments exceeds the predetermined limit; the visual indicator is one or more laser marks that is seen by the operator of the device when the size of the stone fragments exceeds the predetermined limit; the handle includes a movable portion and a fixed portion, the position of the movable portion relative to the fixed portion being the indicator; the indicator is an expandable cone positioned at the distal end of the sheath, the expandable cone being configured to expand as the stone fragments are pulled into the cone with the basket, the expandable cone having a maximum diameter that indicates to the operator that the size of the stone fragments exceeds the predetermined limit; the indicator is an expandable braided sleeve that is configured to be pushed over the stone fragments captured by the basket, the sleeve having a maximum diameter that indicates to the operator that the size of the stone fragments exceeds the predetermined limit; the release mechanism includes a first portion of the plurality of wires and a second portion of the plurality of wires that is rotatable relative to the first portion of the plurality of wires about a longitudinal axis of the sheath, the second portion of the plurality of wires being rotated relative to the first portion of the plurality of wires when the size of the stone fragments exceeds the predetermined limit; the plurality of wires are a plurality of non-woven pre-shaped petals, the plurality of non-woven pre-shaped petals operating as the release mechanism when they expand and release the stone fragments when the size of the stone fragments exceeds the predetermined limit; the plurality of wires are made of shape-memory alloy and the petals are pre-shaped to the closed configuration of the basket; each petal has engagement hooks, the hooks of adjacent petals being engaged when the stone fragments are captured by the basket and the hooks of adjacent petals being unengaged to release the stone fragments when the size of the stone fragments exceeds the predetermined limit; and the basket has a deployed basket configuration with a distal opening sized to limit an acquirable stone fragment size.

In another aspect, the present disclosure provides a method of sizing one or more stone fragments including one or more of the following steps: at least partially surrounding a stone with a stone capture device; utilizing an indicator to determine if the size of the stone fragments exceeds a predetermined limit; and releasing the stone fragments if the size of the stone fragments exceeds the predetermined limit. The method may be further characterized by one or any combination of the features described herein, such as, for example: the indicator is a visual indicator; and the indicator is a tactile indicator.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

The following description is merely exemplary in nature and is not intended to limit the present disclosure, application, or uses.

Figure 1A:
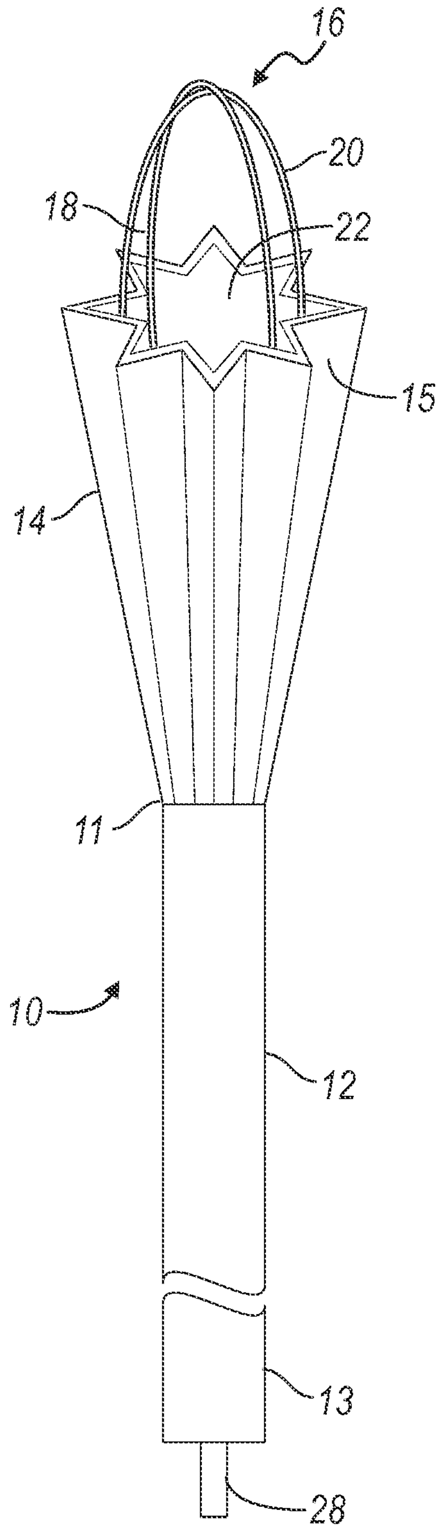
FIG. 1A is a schematic view of a device for capturing stone fragments in accordance with the principles of the present invention.
Figure 1B:
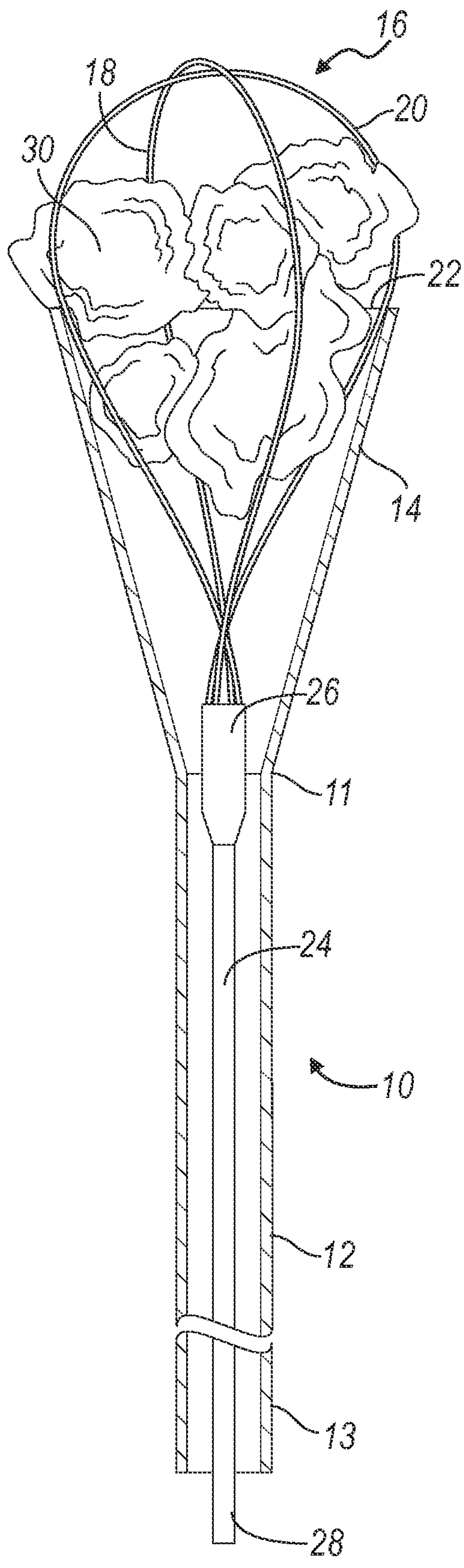
FIG. 1B is a partial cross-sectional view of the device shown in FIG. 1A.

Referring now to the drawings, a medical device for capturing one or more stone fragments is illustrated in FIGS. 1A and 1B and designated at 10. The capturing device 10 includes an outer sheath 12 with a distal end 11 and a proximal end 13. An expandable cone 14 is attached to the distal end 11 of the sheath 12. In certain arrangements, the cone 14 includes a plurality of pleats 14 which enable the cone 14 to expand as one or more stone fragments 30 are pulled into the cone 14.

The capturing device 10 further includes a capturing basket 16 positioned within the sheath 12 and expandable cone 14. The capturing basket 16 includes a rod or handle 24 with a distal end 26 and a proximal end 28. A pair of wires 18 and 20 are attached to the distal end 26 of the handle 24. Specifically, the ends of each of the wires 18 and 20 are attached to the distal end 26 such that the mid region of the wires 18 and 20 intersect at the distal most end of the capturing basket 16. As shown in FIGS. 1A and 1B, the wires 18 and 20 are generally orthogonal to each other at the distal point of intersection.

When the capturing device 10 is in use, the capturing basket 16 is initially collapsed within the cone 14. After, the wires 18 and 20 and cone 14 have been positioned in an anatomical region of a patient containing stone fragments, a user of the capturing device 10, such as, for example, a physician, pushes on the proximal end 28 of the handle 24 such that the wires 18 and 20 exit a distal end 22 of the expandable cone 14. After the stone fragments 30 have been captured by the wires 18 and 20, the physician pulls on the proximal end 28 to draw the stone fragments 30 into the cone 14, which causes the cone 14 to expand. The distal end 22 of the cone 14 is configured to expand to a maximum predetermined size. If the size of the captured stone fragments 30 exceeds this limit, the physician is unable to pull the stone fragments further into the cone 14. The physician then pushes the proximal end 28, which results in the wires 18 and 20 to move away from the cone 14 so that some of the stone fragments can be released. If initially or in subsequent attempts, the size of the stone fragments 30 does not exceed the predetermined size limit of the cone 14, the physician proceeds with retrieving the stone fragments from the patient's anatomy.

Figure 2A:
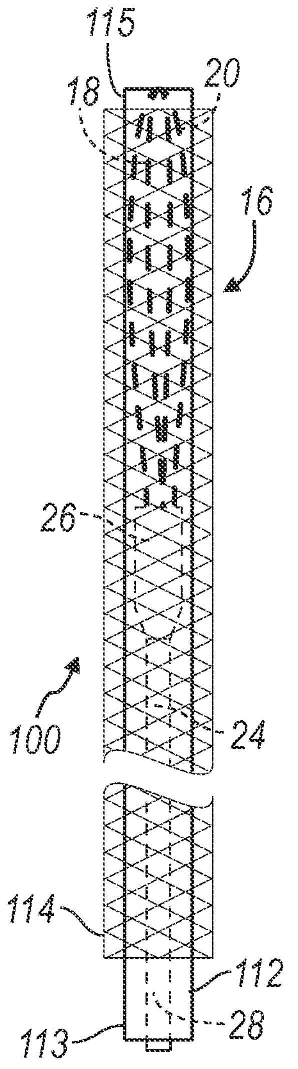
FIGS. 2A-2C are schematic views of another device for capturing stone fragments in accordance with the principles of the present invention.
Figure 2B:
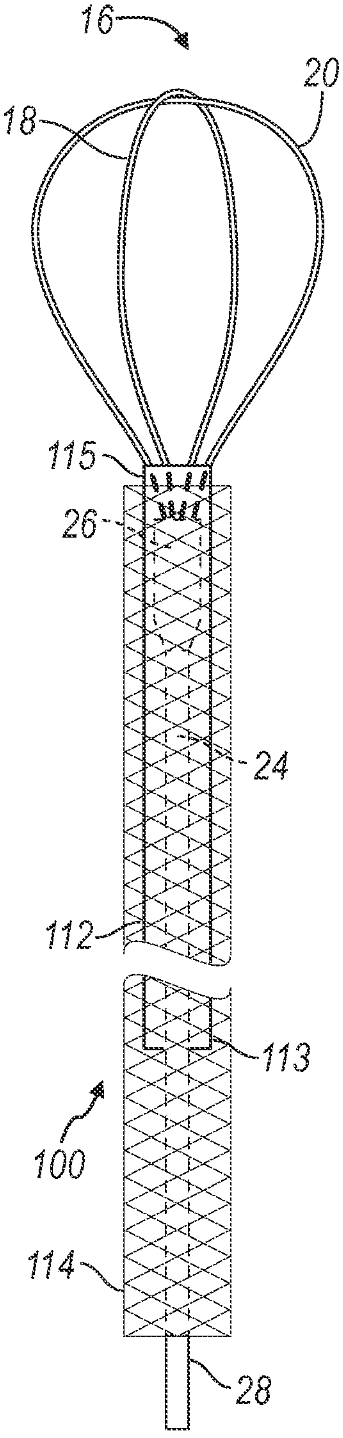
Figure 2C:
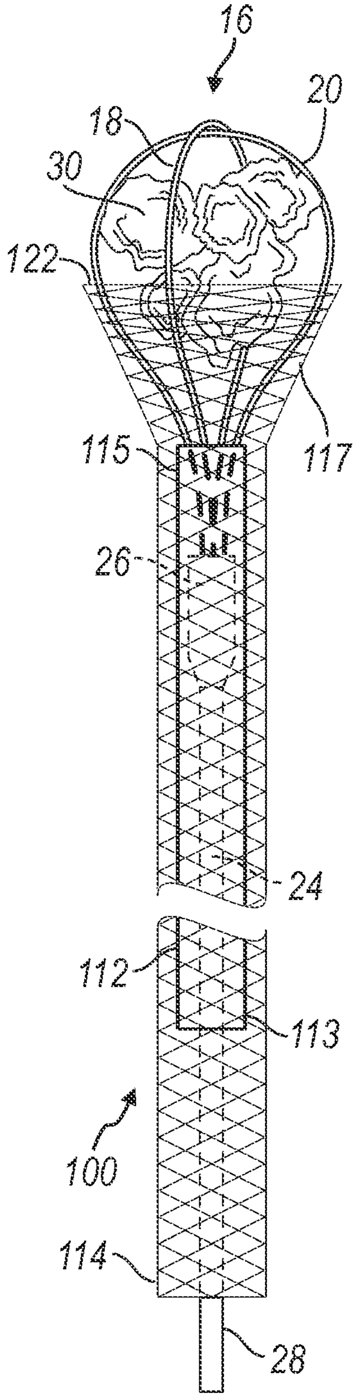

Referring now to FIGS. 2A, 2B and 2C, there is shown a capturing device 100. The capturing device 100 includes the aforementioned capturing basket 16 positioned within a sheath 112 that has a proximal end 113 and a distal end 115. The capturing device 100 further includes a braided sleeve or mesh 114 that slides over the sheath 112 and the capturing basket 16.

When the capturing device 100 is in use, the wires 18 and 20 are initially collapsed within the sheath 112, and the mesh 114 is slid over the sheath 112. A user, such as, for example, a physician, of the capturing device 100 then pushes on the proximal end 28 of the handle 24 such that the wires 18 and 20 are pushed out of the distal end 115 of the sheath 112 to an expanded configuration as shown in FIG. 2B. After one or more stone fragments 20 are captured with the capturing device 16, the physician pulls on the proximal end 28 of the handle 24. Consequently, the stone fragments 30 are pulled into a distal end 122 of the mesh 114, which causes the distal end 122 to expand into a cone-shaped configuration 117 (FIG. 2C). If the accumulation of stone fragments 30 can be pulled through the mesh, then the physician continues to pull on the proximal end 28 of the rod 24 to retrieve the stone fragments 30 from the patient's anatomy. If the distal end 122 of the mesh 114 expands to a maximum limit and the size of the stone fragments exceeds this limit, the physician then pushes on the proximal end 28 of the handle 24 to release some of the stone fragments 30 so that the size of the stone fragments 30 is reduced to a size that allows the stone fragments to be pulled through the mesh 114.

Figure 3A:
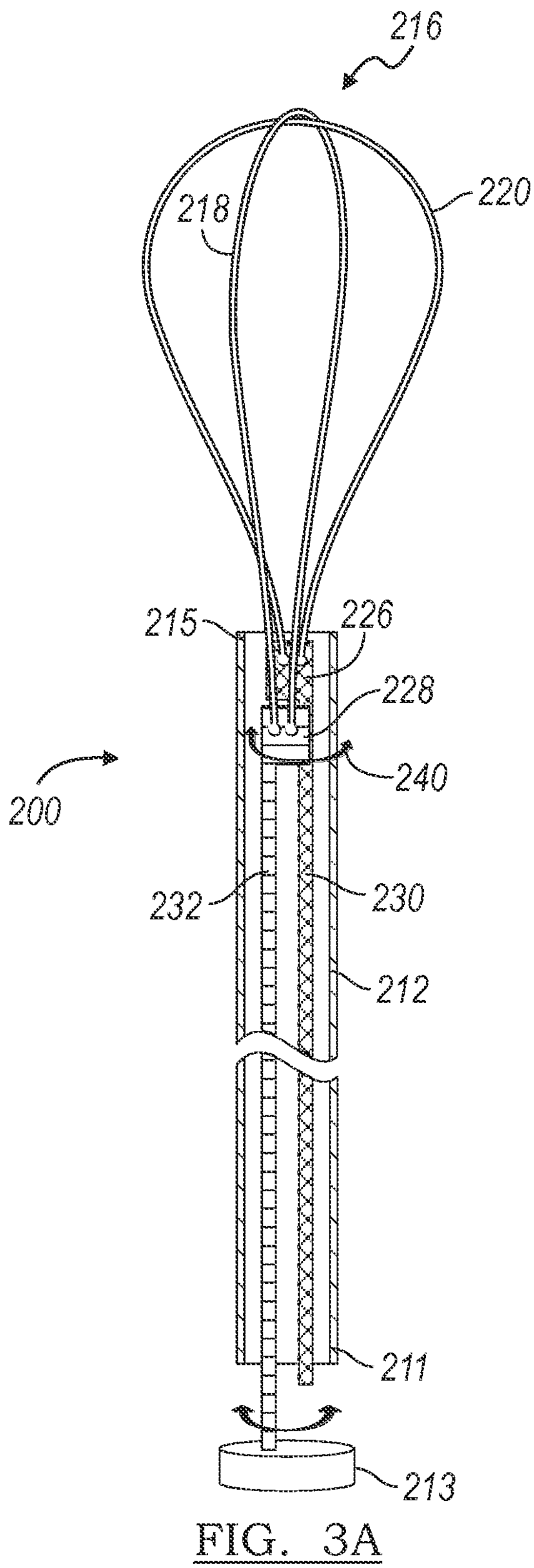
FIGS. 3A-3C are schematic views of yet another device for capturing stone fragments in accordance with the principles of the present invention.
Figure 3B:
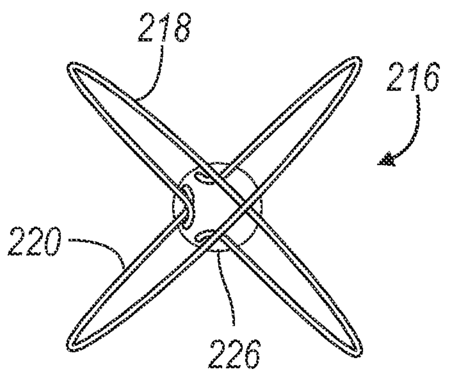

Turning now to FIGS. 3A and 3B, there is shown yet another capturing device 200. The capturing device 200 includes a pair of rods 230 and 232 located within a sheath 212 that has a proximal end 211 and a distal end 215. The capturing device 200 further includes a capturing basket 216 attached to the distal ends 226 and 228 of the rods 230 and 232, respectively. Specifically, the ends of the wire 218 are attached to the distal end 228 of the rod 232, and the ends of the wire 220 are attached to the distal end 226 of the rod 230. The rod 232 is configured to rotate relative to the rod 230 as indicated by the double arrow 240 by turning, for example, a knob 213 connected to the rod 232 and positioned proximally to the proximal end 211 of the sheath 212.

Figure 3C:
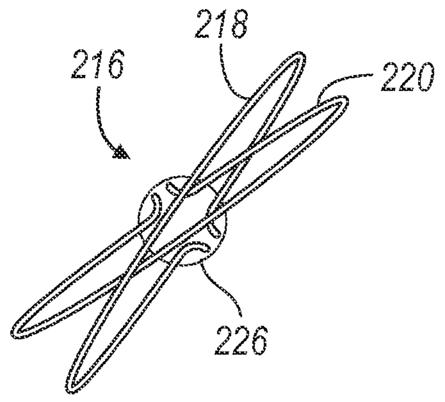

When the capturing device 200 is in use, the wires 218 and 220 are initially collapsed within the sheath 212. The physician then pushes on the knob 213 such that the wires 218 and 220 emerge from the distal end 215 of the sheath 212, resulting in the wires 218 and 220 opening up to an expanded configuration. The physician then turns the knob 213 to rotate the rod 232. Hence, the wire 218 attached to the rod 232 rotates relative to the wire 220 that is attached to the rod 230. Accordingly, the physician can rotate the wire 218 such the wire 218 is orthogonal to the wire 220 in a capture configuration (FIG. 3B) to capture stone fragments, or the wire 218 can be rotated relative to the wire 220 to a release configuration (FIG. 3C) to allow stone fragments to be released from the capture basket 216. Note that when the basket 216 is in the capture configuration, the wires 218 and 220 are oriented orthogonal to each other and define an interior region with a maximum predetermined size limit. Hence, stone fragments with a size that does not exceed this predetermined size limit can be retrieved with the capturing device 200.

Figure 4A:
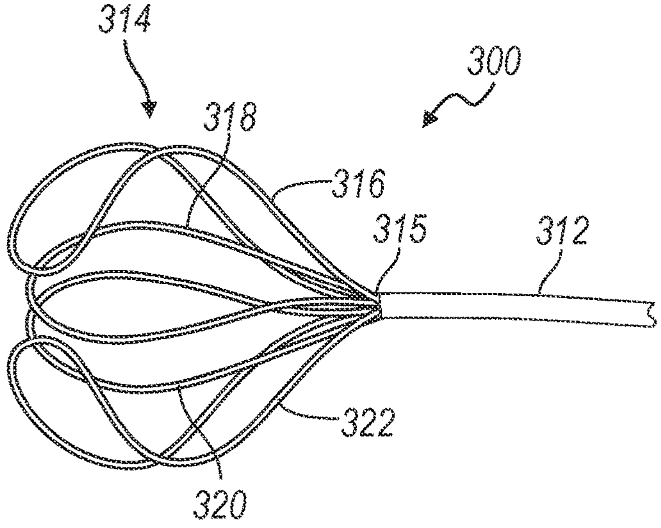
FIG. 4A is a schematic view of yet another device for capturing stone fragments in accordance with the principles of the present invention.
Figure 4B:
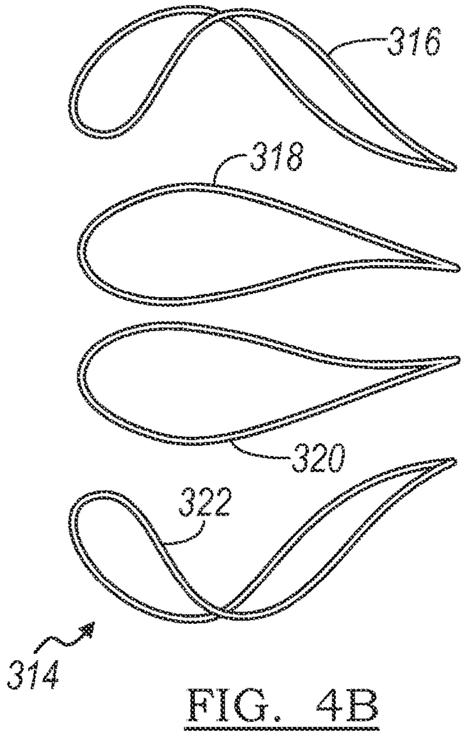
FIG. 4B is a partial expanded view of the device shown in FIG. 4A.

Referring now to FIGS. 4A and 4B, there is shown a capturing device 300 with a rod or handle 312 and a basket 314 attached to a distal end 315 of the handle 312. The basket includes a plurality of petals such as, for example, a set of four non-woven petals 316, 318, 320 and 322. The petals 316, 318, 320 and 322 operate as a release mechanism when they expand and release stone fragments when the size of the accumulated stone fragments exceeds a predetermined size limit. In a particular arrangement, the petals 316, 318, 320 and 322 are made of a shape-memory alloy, such as, for example, Nitinol. The petals 316, 318, 320 and 322 may be pre-shaped to a closed configuration, such that the petals 316, 318, 320 and 322 collapse back to the closed configuration after releasing stone fragments.

Figure 5A:
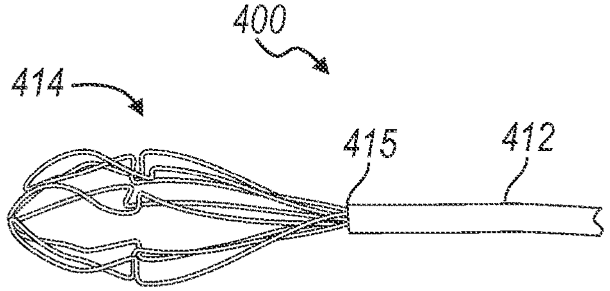
FIG. 5A is a schematic view of yet another device for capturing stone fragments in accordance with the principles of the present invention.
Figure 5C:
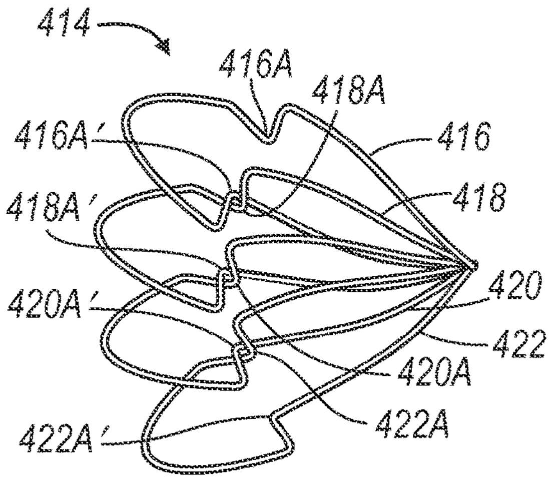
FIG. 5C is a schematic view of engaged petals of the basket shown in FIG. 5A.
Figure 5B:
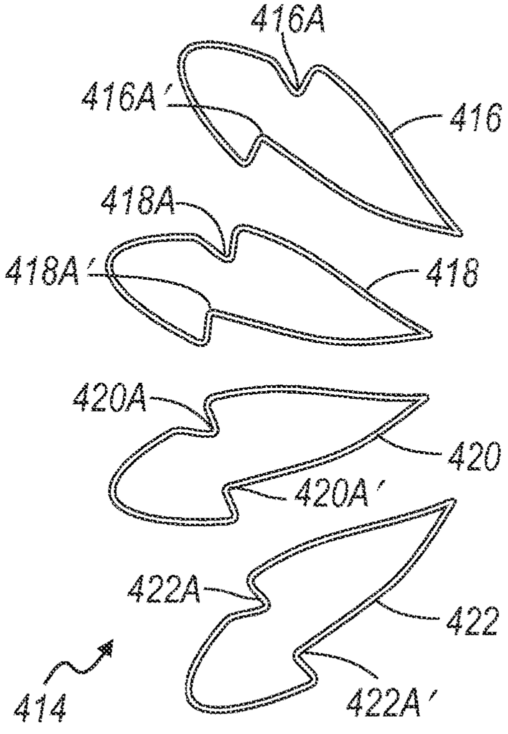
FIG. 5B is a partial expanded view of a basket for the device shown in FIG. 5A.

Referring to FIGS. 5A, 5B and 5C, there is shown a capturing device 400, which is a modification of the capturing device 300. The capturing device 400 includes a rod or handle 412 and a basket 414 attached to a distal end 415 of the handle 412. The basket 414 includes a plurality of petals such as a set of four petals 416, 418, 420 and 422.

The sides of each petal 416, 418, 420 and 422 are configured to engage a side of an adjacent petal. More particularly, the sides of the petals have engagement hooks 416A, 416A', 418A, 418A', 420A, 420A', 422A and 422A' that are configured to engage with an adjacent engagement hook. For example, as shown in FIG. 5C, the engagement hook 416A' is engaged with the engagement hook 418A, the engagement hook 418A' is engaged with the engagement hook 420A, and the engagement hook 420A' is engaged with the engagement hook 422A. The engagement hook 422A' is engaged with the engagement hook 416A to complete the basket structure. Hence, when the capturing device 400 is in use, the hooks 416A, 416A', 418A, 418A', 420A, 420A', 422A and 422A' of adjacent petals are engaged when the stone fragments are captured by the basket 414. The hooks 416A, 416A', 418A, 418A', 420A, 420A', 422A and 422A' become unengaged to release the stone fragments when the size of the stone fragments exceeds a predetermined size limit. In a particular arrangement, the petals 416, 418, 420 and 422 are made of a shape-memory alloy, such as, for example, Nitinol. The petals 416, 418, 420 and 422 may be pre-shaped to a closed configuration, such that the petals 416, 418, 420 and 422 collapse back to the closed configuration after releasing stone fragments.

Figure 6A:
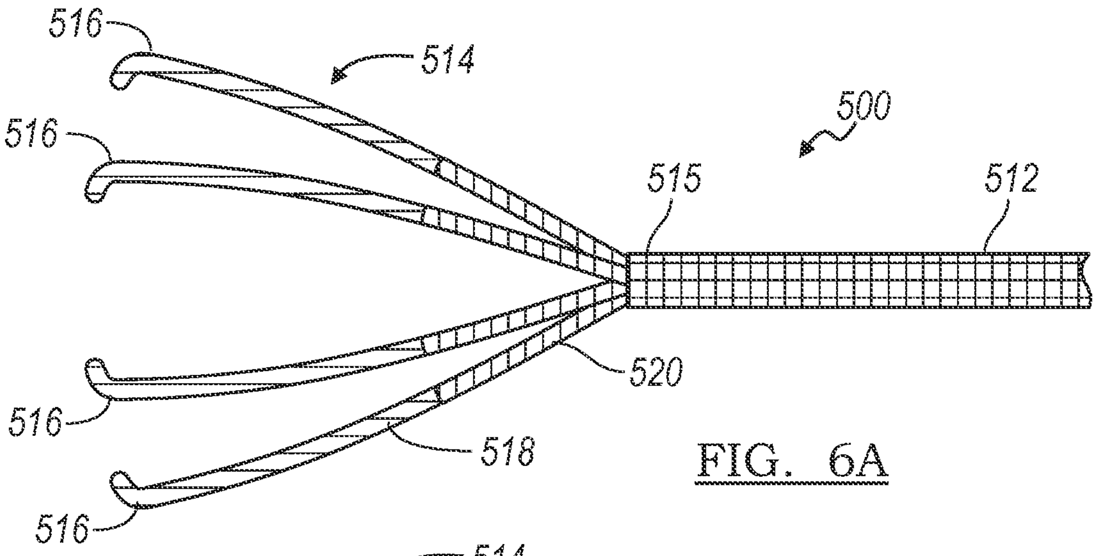
FIG. 6A is a schematic view of yet another device for capturing stone fragments when in an open configuration in accordance with the principles of the present invention.
Figure 6B:
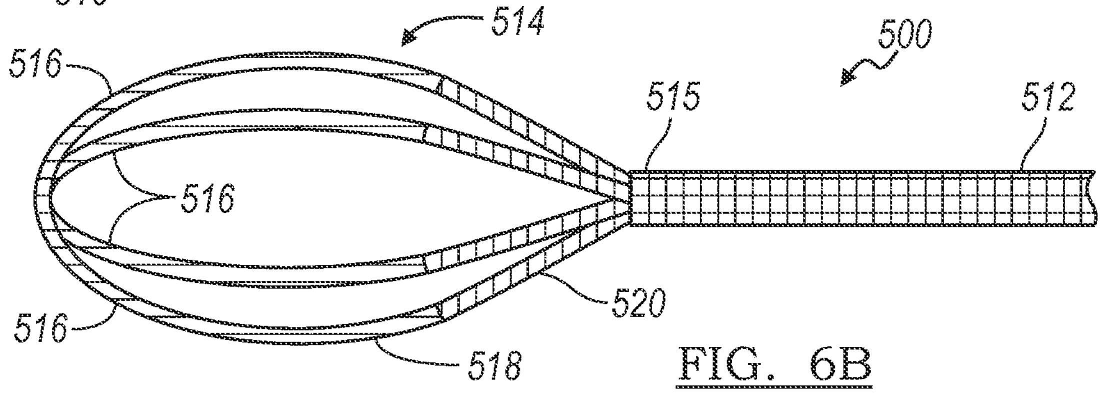
FIG. 6B is a schematic view of the device shown in FIG. 6A in a closed configuration.

Referring now to FIGS. 6A and 6B, there is shown yet another capturing device 500. The capturing device 500 includes a handle or rod 512 and a basket 514 attached to a distal end 515 of the handle 512. The basket 514 includes a plurality of legs such as, for example, a set of four legs 516 shown in FIG. 6A. Each leg 516 has two different markings 518 and 520. The markings 518 and 520 may be two different colors or two different patterns formed on the legs, for example, by laser etching. (Note that such differentiated markings can be used in conjunction with the petals associated with the capturing devices 300 and 400 described previously.)

Accordingly, when the capturing device 500 is in use, the physician is able to view the basket 514 down the length of the handle 512. Hence, when the stone fragments are captured in the basket 514 in a closed configuration (FIG. 6B) or a partially closed configuration, the markings 518 will take up a smaller field of view or some of the markings will be drawn inside the basket sheath 512 and no longer be visible versus when the basket 514 is in a more expanded configuration (FIG. 6A) where the markers take up a larger field of view or more of the markers are visible, which occurs when the size of the captured stone fragments exceed a predetermined size limit.

Figure 7A:
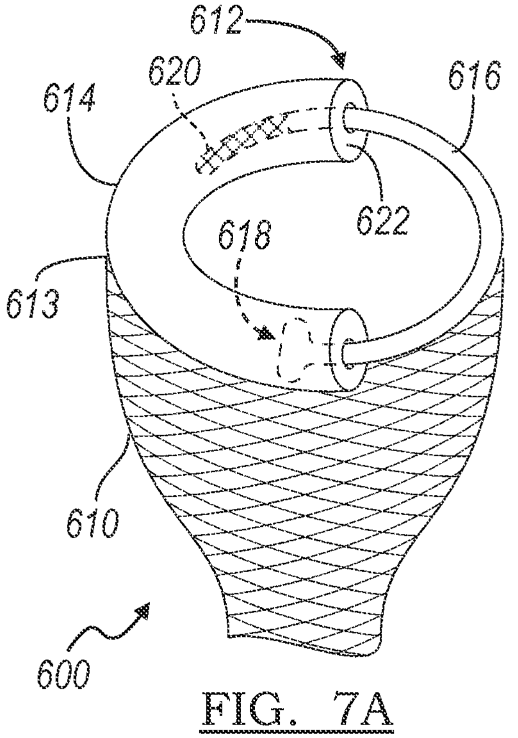
FIGS. 7A and 7B are schematic views of another device for capturing stone fragments in accordance with the principles of the present invention.
Figure 7B:
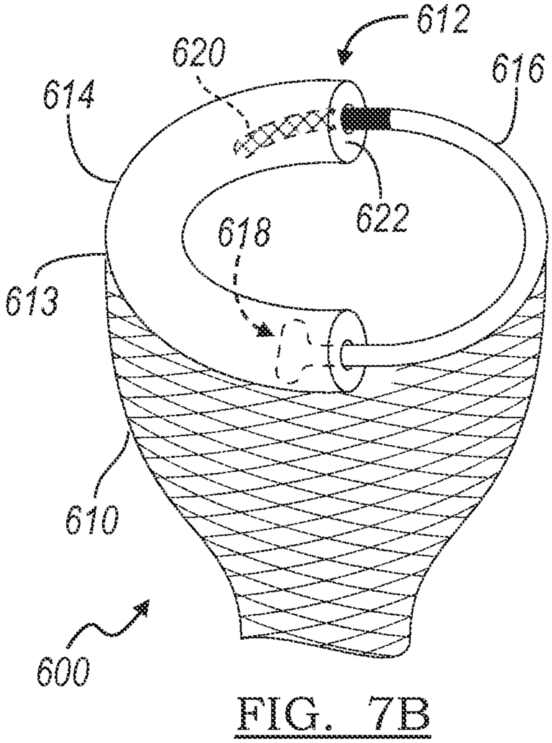

Referring to FIGS. 7A and 7B, there is shown a capturing device 600 that illustrates another type of visual indicator that provides information to the physician when the size of the stone fragments exceed a predetermined size limit. The capturing device 600 includes a mesh or basket 610 and an indicator 612 attached to a distal end 613 of the basket 610. The indicator 612 includes a generally curved and partially hollow portion 614 and a curved solid wire or rod 616. The wire 616 includes an end portion 618 attached to the curved portion 614 and another end portion with markings 620. The wire 616 is able to slide within the hollow interior region of the portion 614. Hence, if the physician cannot see the markings 620 (FIG. 7A) during the capture and retrieval of stone fragments, then the stone fragments captured by the basket 612 do not exceed a predetermined limit. If, however, the markings 620 extend beyond the end 622 of the portion 614 so that the markings 620 are visible to the physician, then the size of the stone fragments exceed the predetermined size limit. In some arrangements of the capturing device 600, the markings 620 are a different color than the rest of the wire 616 and the portion 614. In other arrangements, the markings 620 are formed by laser etching.

Figure 8A:
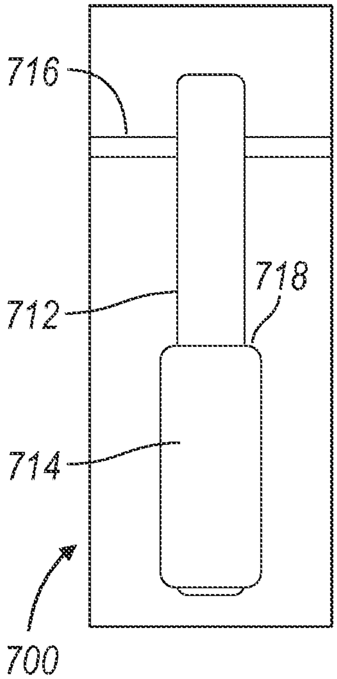
FIGS. 8A-8C are schematic views of a handle portion of yet another device for capturing stone fragments in accordance with the principles of the present invention.
Figure 8B:
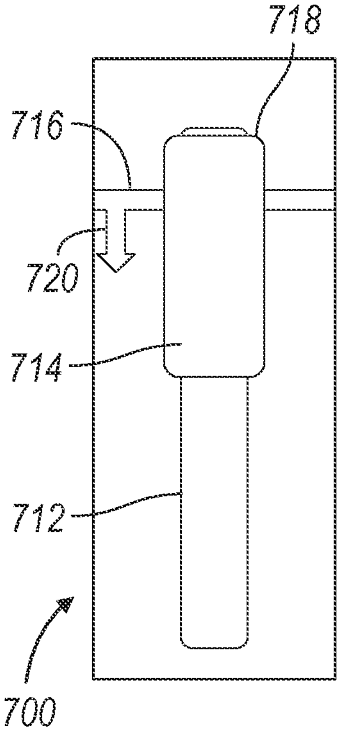
Figure 8C:
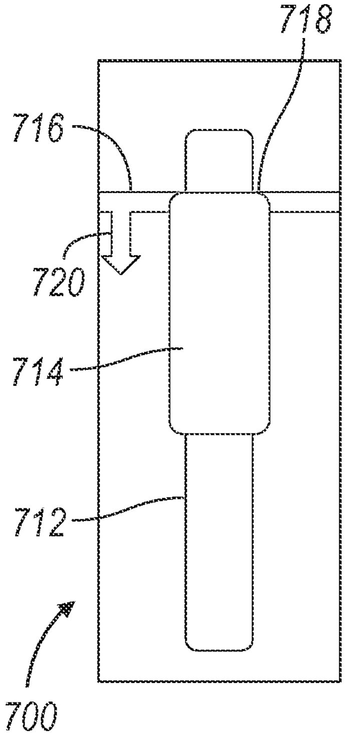

Turning now to FIGS. 8A, 8B and 8C, there is shown a handle portion of a capturing device 700. The handle 700 includes a fixed portion 712 and a movable portion 714 that moves or slides relative to the fixed portion 712. In various arrangements, any one of the aforementioned basket configurations can be fully or partially positioned within the fixed portion 712 and connected to the movable portion 714. Accordingly, as the movable portion 714 is slid or moved upwards (as viewed in the plane of the page) relative to the fixed portion 712, the basket expands to an open configuration, and, as the movable portion 714 is slid downward, the basket closes to a closed configuration, for example, to capture stone fragments. If the physician pulls on the pulls on the movable portion 714 in the direction of the arrow 720 but an end 718 of the movable portion 714 cannot be moved past a visual indicator 716 (FIG. 8B), then the size of the captured stone fragments exceeds a predetermined size limit. On the other hand, if the end 718 lines up with (FIG. 8C) or moves past the indicator 716 in the direction of the arrow 720, then the size of the stone fragments does not exceed the predetermined size limit.

The description of the invention is merely exemplary in nature and variations that do not depart from the gist of the invention are intended to be within the scope of the invention. Such variations are not to be regarded as a departure from the spirit and scope of the invention.

What is claimed is:

1. A medical device for capturing one or more stone fragments, the medical device comprising:

a sheath having a proximal end and a distal end;

a handle at the proximal end of the sheath; and a basket operable with the handle, the basket having a collapsed configuration at times the basket is positioned within the sheath and having a closed expanded configuration at times the basket is positioned beyond the distal end of the sheath, the basket including a plurality of wires that capture the stone fragments;

the plurality of wires forming a first set of petals having a first configuration and a second set of petals having a second configuration different from the first configuration, where the first and second set of petals are configured to expand to another expanded configuration which is larger than the closed expanded configuration to release the stone fragments when a size of the one or more stone fragments exceeds a predetermined limit;

wherein the plurality of wires being able to reset into the closed expanded configuration after releasing the one or more stone fragments.

2. The medical device of claim 1 wherein the medical device further comprises an indicator which comprises a visual indicator on a distal end of the plurality of wires.

3. The medical device of claim 2 where the visual indicator is a color difference that is configured to be seen by the operator of the device when the size of the stone fragments exceeds the predetermined limit.

4. The medical device of claim 2 wherein the visual indicator is one or more laser marks that is configured to be seen by the operator of the device when the size of the stone fragments exceeds the predetermined limit.

5. The medical device of claim 1 wherein the handle includes a movable portion and a fixed portion, the position of the movable portion relative to the fixed portion being an indicator.

6. The medical device of claim 1 wherein the medical device further comprises an indicator which comprises an expandable cone positioned at the distal end of the sheath, the expandable cone being configured to expand as the stone fragments are pulled into the cone with the basket, the expandable cone having a maximum diameter that indicates to the operator that the size of the stone fragments exceeds the predetermined limit.

7. The medical device of claim 1 wherein the medical device further comprises an indicator which comprises an expandable braided sleeve that is configured to be pushed over the stone fragments captured by the basket, the sleeve having a maximum diameter that indicates to the operator that the size of the stone fragments exceeds the predetermined limit.

8. The medical device of claim 1 wherein a first portion of the plurality of wires and a second portion of the plurality of wires that is rotatable relative to the first portion of the plurality of wires about a longitudinal axis of the sheath, the second portion of the plurality of wires being configured to be rotated relative to the first portion of the plurality of wires when the size of the stone fragments exceeds the predetermined limit.

9. The medical device of claim 1, wherein the plurality of wires and petals are made of shape-memory alloy, and wherein the petals are configured to collapse from the another expanded configuration, back to the closed expanded configuration, after the basket releases the one or more stone fragments.

10. The medical device of claim 1 wherein each petal has engagement hooks, the hooks of adjacent petals being configured to engage when the stone fragments are captured by the basket and the hooks of adjacent petals being configured to unengage to release the stone fragments when the size of the stone fragments exceeds the predetermined limit.

11. The medical device of claim 1 wherein the closed expanded configuration comprises a deployed basket configuration with a distal opening sized to limit an acquirable stone fragment size.

12. A medical device for capturing one or more stone fragments, the medical device comprising:

a sheath having a proximal end and a distal end; and a tool extending through the sheath, where the tool comprises a basket at a distal end, where the basket comprises a collapsed configuration when the basket is positioned within the sheath, where the basket comprises a first expanded configuration when the basket is positioned beyond the distal end of the sheath, where the basket comprises a plurality of wires configured to capture the one or more stone fragments, where the plurality of wires form a first set of petals and a second set of petals, where the first and second sets of petals are configured to be collapsed onto the one or more stone fragments from the first expanded configuration and, when a size of the one or more stone fragments exceeds a predetermined limit, the first set of petals and/or the second set of petals are configured to automatically expand to a second expanded configuration which is larger than the first expanded configuration to thereby release the one or more stone fragments, where the plurality of wires are configured to return the basket back to the first expanded configuration after automatically expand and release the one or more stone fragments.

* * * * *